US010245244B2

(12) United States Patent
Yacoub et al.

(10) Patent No.: US 10,245,244 B2
(45) Date of Patent: *Apr. 2, 2019

(54) PHARMACEUTICAL FORMULATIONS FOR THE TREATMENT OF PULMONARY ARTERIAL HYPERTENSION (71) Applicant: HEART BIOTECH PHARMA LIMITED, London (GB)

(72) Inventors: Magdi Habib Yacoub, London (GB); Ibrahim M El Sherbiny, 6th of October (EG)

(73) Assignee: HEART BIOTECH PHARMA LIMITED, London (GB)

( * ) Notice: Subject to any disclaimer, the term of this patent is extended or adjusted under 35 U.S.C. 154(b) by 104 days.

This patent is subject to a terminal disclaimer.

(21) Appl. No.: 14/593,604

(22) Filed: Jan. 9, 2015

(65) Prior Publication Data

US 2015/0196516 A1 Jul. 16, 2015

(30) Foreign Application Priority Data

Jan. 10, 2014 (GB) .................................. 1400412.1

(51) Int. Cl.
*A61K 31/192* (2006.01)
*A61K 31/5575* (2006.01)
*A61K 31/12* (2006.01)
*A61K 9/51* (2006.01)
*A61K 31/4965* (2006.01)
*A61K 9/19* (2006.01)
*A61K 9/50* (2006.01)

(52) U.S. Cl.
CPC .............. *A61K 31/192* (2013.01); *A61K 9/19* (2013.01); *A61K 9/5036* (2013.01); *A61K 9/5146* (2013.01); *A61K 9/5153* (2013.01); *A61K 9/5161* (2013.01); *A61K 31/12* (2013.01); *A61K 31/4965* (2013.01); *A61K 31/5575* (2013.01)

(58) Field of Classification Search
None
See application file for complete search history.

(56) References Cited

U.S. PATENT DOCUMENTS

| 8,481,479 | B1 | 7/2013 | Mousa | |
| 2004/0147466 | A1* | 7/2004 | Barman | A61K 48/0041 514/44 R |
| 2008/0286372 | A1 | 11/2008 | Pacetti et al. | |
| 2011/0118200 | A1* | 5/2011 | Hu | C08B 37/003 514/34 |
| 2011/0229580 | A1* | 9/2011 | Srivastava | A61K 9/1652 424/493 |
| 2011/0250134 | A1 | 10/2011 | Cabrales | |
| 2015/0328232 | A1* | 11/2015 | Malinin | A61K 9/0075 424/489 |

FOREIGN PATENT DOCUMENTS

| EP | 2679227 A1 | 1/2014 | |
| WO | WO 2010007604 A2 * | 1/2010 | .......... A61K 9/0075 |
| WO | 2013/123492 A2 | 8/2013 | |

OTHER PUBLICATIONS

L.C. Price et al., "Dexamethasone reverses monocrotaline-induced pulmonary arterial hypertension in rats," Eur Respir J 2011; 37: 813-822.*
I.M. El-Sherbiny et al., "Swellable Microparticles as Carriers for Sustained Pulmonary Drug Delivery," Journal of Pharmaceutical Sciences, vol. 99, No. 5, May 2010, pp. 2343-2356.*
A. Popat et al., "A pH-responsive drug delivery system based on chitosan coated mesoporous silica nanoparticles," J. Mater. Chem., 2012, 22, 11173-11178.*
M. George et al., "pH sensitive alginate-guar gum hydrogel for the controlled delivery of protein drugs," International Journal of Pharmaceutics 335 (2007) 123-129.*
M. Malhotra et al., "A novel method for synthesizing PEGylated chitosan nanoparticles: strategy, preparation, and in vitro analysis," International Journal of Nanomedicine 2011: 6, 485-494.*
Lee, "Treatment of blood flow abnormality using mucosal delivery of nitric oxide," Drug Delivery and Translational Research, vol. 1, No. 3, pp. 201-208, (Apr. 30, 2011) XP055187213.
Extended European Search Report, dated May 15, 2015, issued in corresponding European Application No. 15150623.5.
UK Search Report, dated Jul. 15, 2014, issued in priority UK Application No. GB1400412.1.
El-Sherbiny et al., Molecular Pharmaceuticals, vol. 9, No. 2, pp. 269-280 (2012).
Gessler et al., Therapeutic Advances in Respiratory Disease, vol. 5, No. 3, pp. 195-206 (2011).
Akagi et al., Circulation, vol. 128, No. 22, p. 15695 (2013) (abstract).

\* cited by examiner

*Primary Examiner* — Monica A Shin
(74) *Attorney, Agent, or Firm* — Saul Ewing Arnstein & Lehr LLP (57) ABSTRACT

Pharmaceutical formulations are described for use in the treatment of pulmonary arterial hypertension (PAH). The formulations comprise polymeric nanoparticles encapsulated within crosslinked polymeric hydrogel microparticles, wherein the polymeric nanoparticles carry a therapeutic agent suitable for treatment of PAH loaded within them (for example, prostacyclin synthetic analogs, PPAR β agonists and NO donors). Preferred formulations are inhalable, dry powder pharmaceutical formulations, which are able to swell on administration to the lungs of a patient.

21 Claims, 5 Drawing Sheets

Figure 1. Synthesis of the PEG-CS copolymer

Figure 2. Synthesis of (a) PEG-CS-Oleic, and (b) PEG-CS-Cholanic copolymer

PHARMACEUTICAL FORMULATIONS FOR THE TREATMENT OF PULMONARY ARTERIAL HYPERTENSION

CROSS-REFERENCE TO RELATED APPLICATIONS

This application is based on and claims priority to United Kingdom Application No. 1400412.1, filed on Jan. 10, 2014, the entire contents of which is fully incorporated herein by reference.

FIELD OF THE INVENTION

The present invention relates to pharmaceutical formulations for the treatment of pulmonary arterial hypertension (PAH). Aspects of the invention relate to inhalable, dry powder formulations for pulmonary administration. Further aspects of the invention relate to formulations suitable for injectable or oral administration.

BACKGROUND TO THE INVENTION

Pulmonary arterial hypertension (PAH) is a rare but devastating disease, in which the normally low pulmonary artery pressure becomes elevated due to vaso-constriction and to the remodelling of pulmonary vessels. This in turn increases workload on the right side of the heart, causing right heart hypertrophy, fibrosis and ultimately heart failure.

Interventions used in the management of PAH are traditionally targeted on the vasculature, with the aim of enhancing vasodilation and anti-proliferation pathways. These include the prostacyclin analogues and nitric oxide (NO). However, it is increasingly recognized that in addition to the pulmonary vasculature, the right heart is also a viable therapeutic target in the treatment of PAH. PPAR β inhibitors have been shown in recent studies on animal models to reduce right heart hypertrophy without influencing pulmonary vascular remodelling.

Prostacyclin Analogues

Prostacyclin is a powerful vasodilator, produced in the body by endothelial cells. Patients with PAH are found to have low levels of prostacyclin, leading to a frequently life-threatening constriction of the pulmonary vasculature.

Natural prostacyclin has been found to be unstable in solution, and undergoes rapid degradation, making it very difficult to use for clinical applications. Over 1,000 synthetic prostacyclin analogues have been developed to date as a result. One of these, Treprostinil has demonstrated unique effectiveness in inhibiting platelet activation and as a vasodilator, and it has relatively good stability in solution compared to native prostacyclin. Other prostacyclin analogues, such as Selexipag are currently undergoing clinical trials with highly encouraging results.

Treprostinil is currently marketed in two formulations, as an infusion (subcutaneous or intravenous via a continuous infusion pump), or as an inhaled aerosol, used with a proprietary device, 4 times per day and at least 4 hours apart. The infusion is frequently associated with side effects such as severe site pain or reaction, whilst the aerosol requires a disciplined regimen on the part of patients. Attempts to develop an oral formulation have to date failed FDA regulatory approval due to the relatively adverse risk/efficiency ratio of prototypes tried so far.

Developing alternative formulations of Treprostinil, which bypass the many serious shortcomings of the continuous infusion/pump system, and which allow efficient, controlled, targeted and sustained release of the drug without the complexity of the current aerosol system, should improve patient compliance and experience of treatment, and ultimately impact on successful management of the condition.

Selexipag is currently undergoing Phase III trials. Selexipag is designed to act on IP (prostacyclin) receptors selectively, and has to date demonstrated a significant reduction in pulmonary vascular resistance within the trial cohorts studied. It is currently produced as an oral formulation, and although the administration regime is far simpler than for Treprostinil, again the development of a formulation and delivery mechanism that allows efficient, controlled, targeted and sustained release of the drug would significantly reduce side effects and improve patient compliance, ultimately impacting positively on outcome.

Nitric Oxide

Nitric oxide is known to have vasodilatory effects on the pulmonary vasculature in both humans and animals. A number of trials suggest that the effects of NO on vascular resistance are selective (ie focused on pulmonary rather than systemic), and do not cause systemic hypotension or raise methaemoglobin.

The main challenge with NO therapy is in sustaining benefit over a prolonged period. A delivery mechanism that allows controlled, sustained release of NO, such as that offered by the present invention, can substantively overcome this challenge. Formulations of NO donors (such as, but not limited to, organic nitrates, nitrite salts, s-nitrosoglutathione (GSNO), and S-Nitrosothiols) can be loaded into the delivery mechanism, which can produce sustained and controlled doses of NO when activated by the moisture in the lung.

PPAR β Agonists

The pulmonary vasoconstriction and remodelling associated with PAH lead to overloading and hypertrophy of the right heart, and eventually to heart failure. While focusing on vasodilatation is an important part of effective management of PAH, it is increasingly apparent that the hypertrophic right heart is also a valid therapeutic target for intervention in the disease.

The PPARs (peroxisome proliferator activated receptors) have been shown in studies to be an attractive protective pathway in the overloaded heart. As well as protecting against ischemia reperfusion injury, in mice, PPAR has demonstrated effects on reducing left ventricular dilation, fibrosis and mitochondrial abnormalities. GW0742, a ligand which activates PPAR β selectively, has been shown in studies to reduce right heart hypertrophy without influencing pulmonary vascular remodelling. GW0742 is not currently used in the treatment of PAH. Nonetheless it is a feature of this invention that suitable formulations of GW0742 can be developed for loading into nano-particle delivery systems for lung, oral and intravascular administration.

Current treatments for PHA require that the therapy is administered by injection, or by inhalation. Inhalation would typically be preferred over injection, but current inhalable therapies require complex administration forms and schedules, and this has an effect on patient compliance or ease of delivery. Some therapeutics (for example, NO donors) require sustained release for effective administration.

The present invention proposes alternative formulations, which in some embodiments would be easier to administer.

BRIEF SUMMARY OF THE INVENTION

According to a first aspect of the present invention, there is provided an inhalable, dry powder pharmaceutical formulation for the treatment of pulmonary arterial hypertension (PAH), the formulation comprising polymeric nanoparticles encapsulated within crosslinked polymeric microparticles, wherein the polymeric nanoparticles carry a therapeutic agent suitable for treatment of PAH loaded within them.

By "nanoparticle" is meant a composition having a mean particle size (preferably diameter) of less than 600 nm, preferably less than 500 nm. Preferably the mean diameter ranges from 1 to 500 nm, more preferably 10-250 nm. In preferred embodiments, the mean diameter is less than 250 nm, preferably less than 200 nm.

By "microparticle" is meant a composition having a mean particle size (preferably diameter) ranging from 0.75 to 10 μm. Preferred mean particle size ranges include 0.75 to 7.5 μm, 1 to 5 μm, 2 to 4 μm. Most preferred range is 1 to 5 μm.

The mean particle size may be determined by any suitable method practiced in the art; examples of suitable methods are exemplified herein.

The nanoparticle plus microparticle formulation described herein may be referred to as a nano-micro-carrier, or nano-micro-particles, or nano-micro formulation.

The present formulations provide therapeutic routes for treatment of PAH which are simpler to administer than existing treatments. This is achieved by incorporating the drug into nanoparticles. However, nanoparticles themselves are difficult to administer by inhalation, so these are then incorporated into crosslinked polymeric microparticles. This makes the formulation suitable for dry powder inhalation. The nanoparticles encapsulate and stabilise the drug, while also allowing for pulmonary delivery due to their size. The microparticles can help to make the physical form more suitable for one or another administration route, while also permitting sustained release of the nanoparticles.

The nanoparticles and microparticles are preferably biodegradable, and are preferably biocompatible. By biodegradable is meant that the particles will break down naturally within the body under physiological conditions; preferably the conditions as found within the lung. By biocompatible is meant that the particles will not elicit an immune response from the patient. The nanoparticles preferably biodegrade under physiological conditions to give a drug release rate of 0.1-0.3 w % per hour.

The polymeric nanoparticles preferably comprise a chitosan or a chitosan-derivative polymer. Suitable chitosan-derivative polymers include chitosan-PEG, N-trimethyl chitosan, and/or chitosan derivatives having hydrophobic side chains (for example, stearic acid, cholanic acid, phthaloyl, butyl acrylate). Alternatively, the nanoparticles may comprise a copolymer, preferably an amphiphilic copolymer, for example, poly(lactic-co-glycolic acid) (PLGA). In preferred embodiments, the nanoparticles are graft and block copolymers. Chitosan or chitosan derivatives are particularly preferred, due to chitosan's ability to enhance absorption in lung tissues through opening the intercellular tight junctions of the lung epithelium. We refer to this ability herein as "epithelial targeting", and this feature also makes similar formulations suitable for administration to other epithelial tissues, for example, the intestine. Thus, in preferred embodiments, the nanoparticles are epithelially targeted.

The polymeric nanoparticles in preferred embodiments have a moisture content, in the dry formulation, of less than 2%.

The polymeric nanoparticles may be produced via emulsion polymerization, ionotropic gelation, polyelectrolyte complexation, and/or self-assembly. In preferred embodiments, the nanoparticles may be produced via self assembly following sonication of amphiphilic polymer solutions.

The cross-linked polymeric microparticles preferably comprise cross-linked hydrogel polymers, and are preferably crosslinked hydrogel microparticles. These may be in the form of semi-interpenetrating polymeric networks (semi-IPNs) and full-IPNs. These semi- and full-IPNs are preferably based on natural polymers such as, but not limited to, chitosan and water soluble chitosan derivatives (such as carboxymethyl and PEGylated derivatives) in a combination with one or more of nontoxic, biocompatible, and biodegradable polymers including, but not limited to, hyaluronate, carrageenan and oligoguluronate. In some embodiments, only chitosan or chitosan derivatives are used. The semi-IPN and IPN microparticles are crosslinked through any suitable method, including ionotropic gelation, polyelectrolyte complexation and/or H-bonding. The nanoparticles-microparticles formulations may be produced using a spray-drying technique, spray gelation, or ionotropic gelation followed by lyophilization. Spray drying is preferred.

The microparticles are preferably swellable; more preferably the microparticles are hydrogel microparticles and the hydrogel is swellable. This allows the hydrogel to absorb moisture from the lung or other delivery site and so permit release of the nanoparticles. The hydrogel is preferably able to swell to at least 200, 300, 400, 500% of the original (dry formulation) size. In a preferred embodiment, a microparticle of 2-5 μm dry diameter is able to swell to at least 20 μm diameter. The microparticle is preferably able to swell to the larger diameter within 10, 9, 8, 7, 6, 5, 4, 3, or 2 minutes from administration to the lungs of a patient. In a further preferred embodiment, the microparticle is able to swell to at least 10 times the dry size within 3 minutes from administration.

The hydrogel preferably comprises less than 10%, preferably less than 7.5%, more preferably less than 5, 4, 3, 2% water when in the dry formulation. In preferred embodiments, this is less than 2%.

The particles preferably biodegrade under physiological conditions (3-5% weight loss per day) to give a drug release rate of less than 1% per hour, more preferably less than 0.5% per hour. In preferred embodiments, the drug release rate is 0.1-0.3 w % per hour.

The microparticles may comprise a pH responsive carrier. Smart pH-responsive particles for drug delivery are known, and are used in situations where it is desirable to release a drug from a carrier under certain pH conditions; for example, when the carrier is in a specific environment, such as the intestine. Examples of the preparation and use of pH-responsive carriers are given in PS Stayton and AS Hoffman, "Smart pH-responsive carriers for intracellular delivery of biomolecular drugs", in V Torchilin (ed), Multifunctional Pharmaceutical Nanocarriers, Springer Science and Business Media, 2008; and in Stephanie J. Grainger and Mohamed E. H. El-Sayed, "STIMULI-SENSITIVE PARTICLES FOR DRUG DELIVERY", in Biologically Responsive Hybrid Biomaterials, Esmaiel Jabbari and Ali Khademhosseini (Ed), Artech House, Boston, Mass., USA.

The therapeutic agent is preferably selected from prostacyclin synthetic analogs, PPAR β agonists and NO donors. The prostacyclin synthetic analog may be treprostinil or selexipag. The PPAR β agonist may be GW0742. In preferred embodiments, the agent is a prostacyclin synthetic analog, most preferably treprostinil.

The dosage of the therapeutic agent may be selected depending on the desired administration dose to the patient, and may vary depending on the agent to be used, and the composition of the nano and microparticles.

According to a further aspect of the invention, there is provided a composition comprising polymeric nanoparticles encapsulated within crosslinked polymeric microparticles, wherein the polymeric nanoparticles carry a therapeutic agent suitable for treatment of PAH loaded within them, for use in the treatment of pulmonary arterial hypertension (PAH). The invention also provides the use of a composition comprising polymeric nanoparticles encapsulated within crosslinked polymeric microparticles, wherein the polymeric nanoparticles carry a therapeutic agent suitable for treatment of PAH loaded within them in the manufacture of a medicament for the treatment of PAH.

A further aspect of the invention provides a method of treatment of PAH, the method comprising administering a composition comprising polymeric nanoparticles encapsulated within crosslinked polymeric microparticles, wherein the polymeric nanoparticles carry a therapeutic agent suitable for treatment of PAH loaded within them to a patient in need thereof, wherein the composition is administered by inhalation.

A further aspect of the invention provides a pharmaceutical formulation comprising polymeric nanoparticles encapsulated within smart pH-responsive crosslinked polymeric microparticles, wherein the polymeric nanoparticles carry a therapeutic agent selected from prostacyclin synthetic analogs, PPAR β agonists and NO donors loaded within them, wherein the pH-responsive microparticles are targeted to the intestine, and wherein the nanoparticles are targeted to the epithelium. This aspect of the invention may be suitable for intestinal or oral administration, for example. Smart pH-responsive particles for drug delivery are known, and are used in situations where it is desirable to release a drug from a carrier under certain pH conditions; for example, when the carrier is in a specific environment, such as the intestine. Examples of the preparation and use of pH-responsive carriers are given in PS Stayton and AS Hoffman, "Smart pH-responsive carriers for intracellular delivery of biomolecular drugs", in V Torchilin (ed), Multifunctional Pharmaceutical Nanocarriers, Springer Science and Business Media, 2008; and in Stephanie J. Grainger and Mohamed E. H. El-Sayed, "STIMULI-SENSITIVE PARTICLES FOR DRUG DELIVERY", in Biologically Responsive Hybrid Biomaterials, Esmaiel Jabbari and Ali Khademhosseini (Ed), Artech House, Boston, Mass., USA.

A yet further aspect of the invention provides an injectable pharmaceutical formulation comprising polymeric nanoparticles carrying a therapeutic agent selected from prostacyclin synthetic analogs, PPAR β agonists and NO donors loaded within them, and wherein the nanoparticles are targeted to the epithelium. For injectable formulations, it may not be beneficial to provide microparticles, and the nanoparticles may be injected directly. Although not preferred for treatment of PAH, such formulations may find application where inhalation is not practical for one reason or another, or where sites other than the lungs are to be targeted.

DETAILED DESCRIPTION OF THE INVENTION

The present invention provides novel formulations of therapeutics for the treatment of PAH. Preferred therapeutic agents include prostacyclin synthetic analogs, PPAR β agonists and NO donors. The agents are incorporated into biodegradable polymeric nanoparticles, which themselves are incorporated into hydrogel microparticles or smart pH-responsive microparticles.

Background art which may be of benefit in understanding the invention includes:

El-Sherbiny, I. M., & Smyth, H. D. C. (2012). Controlled release pulmonary administration of curcumin using swellable biocompatible nano-microparticles systems. Molecular Pharmaceutics, 9(2), 269-280.

El-Sherbiny I M, and Smyth, H D C. (2010) Biodegradable nano-micro carrier systems for sustained pulmonary drug delivery: (I) self-assembled nanoparticles encapsulated in respirable/swellable semi-IPN microspheres. Int J. Pharm 395: 132-141.

El-Sherbiny I M, Mcgill S, and Smyth H D C. (2010) Swellable microparticles as carriers for sustained pulmonary drug delivery. J. Pharm Sci, 99(5): 2343-2356.

El-Sherbiny I M, and Smyth H D C. (2010) Novel cryomilled physically crosslinked biodegradable hydrogel microparticles as carriers for inhalation therapy. J. Microencapsulation, 27(7): 561-572.

El-Sherbiny I M, Abdel-Mogibb M, Dawidar A, Elsayed A, and Smyth H D C. (2010) Biodegradable pH-responsive alginate-poly(lactic-co-glycolic acid) nano/micro hydrogel matrices for oral delivery of silymarin, CarbohydrPolym, 83, 1345-1354.

El-Sherbiny I M, and Smyth H D C. (2010) PLGA nanoparticles encapsulated in respirable/swellable hydrogel microspheres as potential carriers for sustained drug delivery to the lung. Annual Meeting of American Association of Pharmaceutical Scientists, New Orleans, La.

El-Sherbiny I M, and Smyth H D C. (2010) Nano-micro carrier systems for sustained pulmonary drug delivery. Biomedical Engineering Society Annual Meeting (BMES), Austin, Tex.

Selvam P, El-Sherbiny I M, and Smyth H D C. (2010) Swellable microparticles for sustained release drug delivery to the lung using propellant driven metered dose inhalers. Biomedical Engineering Society Annual Meeting (BMES), Austin, Tex.

El-Sherbiny I M, and Smyth H D C. (2010) Novel non-covalently crosslinked hydrogel nano-microparticles for inhalation therapy. Annual Meeting of American Association of Pharmaceutical Scientists, New Orleans, La.

El-Sherbiny I M, and Smyth H D C. (2009) Cryomilled physically crosslinked biodegradable hydrogel microparticles as novel potential carriers for inhalation therapy.

Annual Meeting of American Association of Pharmaceutical Scientists, Los Angles, Calif., AM-09-01692.

El-Sherbiny I M, and Smyth H D C. (2009) Novel spray dried biodegradable semi-IPN hydrogel microspheres for pulmonary drug delivery. Annual Meeting of American Association of Pharmaceutical Scientists, Los Angeles, Calif., (AM-09-01708).

Reference to these publications should not be taken as an admission that the contents of any particular document are relevant prior art. However, the skilled person is referred to each of these publications for details of ways in which nanoparticles and/or microparticles may be produced.

Various preliminary studies (referred to in the citations listed above) performed with regard to options for inhalation, and oral therapy support the proposal that polymeric nanoparticles and/or nanoparticles-microparticles carrier systems will improve bioavailability, increase targeting, reduce dose frequency, avoid macrophage clearance and confer sustained delivery of therapeutic agents to the lung compared to free drugs. Remarkably, the preliminary data has shown that:

(1) The loading of drugs into polymeric nanoparticles has the potential to significantly enhance dissolution and absorption, and consequently can improve the bioavailability of the loaded drugs.

(2) drug-loaded nanoparticles can be incorporated into novel crosslinked microparticles with physicochemical characteristics (aerodynamic size, shape, moisture content, etc) appropriate for inhalation therapy.

(3) the design and composition of the nanoparticles-microparticles carriers can be modulated to allow them to absorb moisture and expand rapidly to evade endocytosis by macrophage cells.

(4) biodegradation rates of the developed carriers are controllable.

(5) the polymeric nanoparticles-microparticles systems can be used efficiently for dry powder inhalation therapy.

(6) crosslinked polymeric microparticles incorporating drug-loaded nanoparticles can efficiently confer sustained release of these drugs once deposited in the lung.

Hypothesis

The hypothesis underlying this invention is that the development of appropriate respirable crosslinked polymeric nano-microparticle systems will enhance bioavailability, increase deep lung targeting, reduce dose frequency, avoid macrophage clearance and confer sustained pulmonary delivery of Prostacyclin analogues, Nitric Oxide and PPAR β agonists for the treatment of pulmonary arterial hypertension (PAH) compared to free drugs. Also, that the formulation of the above into pre-designed biodegradable and biocompatible smart pH-responsive hydrogel particles will improve bioavailability, reduce dose frequency, increase targeting, and confer sustained oral and intravascular delivery of these interventions compared to free drugs.

1. Composition of Nanoparticles

Our preliminary studies showed that incorporation of drug-loaded nanoparticles into respirable crosslinked microparticles can allow for additional control of drug action and release. Also, in our preliminary investigations, we found that loading of hydrophobic active ingredients into nanoparticles (made of ubiquitous polymers such as PLGA) considerably enhances the dissolution/absorption of these ingredients. Building on these observations, a new series of specifically designed polymeric nanoparticles were obtained via self assembly of a new series of amphiphilic graft and block copolymers. The developed graft and block copolymers are based on natural polymers and chemically modified natural polymers such as, but not limited to, chitosan, chitosan derivatives, alginate, carrageenan, and cellulose derivatives.

Materials: The amphiphilic copolymers were produced via chemical modifications of some natural polymers such as, but not limited to, chitosan and chitosan derivatives through introducing of hydrophilic side chains (such as PEG) and/or hydrophobic moieties (mainly, stearic acid, cholanic acid, phthaloyl, and butyl acrylate). Chitosan, a cationic biopolymer obtained through alkaline N-deacetylation of chitin, has been selected as a preferred base polymer for the development of the nanoparticles due to its numerous desirable characteristics including biodegradability, non-toxicity, biocompatibility, in addition to its ability to enhance drug absorption in lung tissues through opening the intercellular tight junctions of the lung epithelium (see Parka J H, Kwon S, Lee M, Chung H, Kim J H, Kim Y S, Park R W, Kim I S, Seo S B, Kwon I C, and Jeong S Y. (2006) Self-assembled nanoparticles based on glycol chitosan bearing hydrophobic moieties as carriers for doxorubicin: in vivo biodistribution and anti-tumor activity. Biomaterials, 27: 119-126).

Preparation Method: The self-assembled polymeric nanoparticles were prepared with (and without) sonication of different concentrations of the modified polymer solutions at different sonication powers (30-75 W) for different intervals. The effect of relative compositions plus the different preparation parameters onto the physicochemical characteristics (mainly particle size) of the resulting nanoparticles were investigated extensively, to ensure desired properties have been achieved.

Drug loading: The nanoparticles of different architectures loaded with the bioactive moieties (treprostinil, Selexipag, PPAR β agonists or NO donor) were prepared in the same manner used for plain nanoparticles. Then, the effect of relative compositions plus the different preparation parameters onto both drug loading capacity and loading efficiency (%) of the produced nanoparticles were studied in detail to determine optimal loading.

2. Nanoparticle Characterization

Polymer Characterization: The synthesized and chemically modified polymers used as pre-cursors for the nanoparticles were characterized using different analytical tools such as elemental analysis, FT-IR, differential scanning calorimetry (DSC), and thermogravimetric analysis (TGA). Also, the crystallography patterns of powdered modified polymers were investigated by X-ray diffraction (XRD).

Physicochemical characterization of the developed nanoparticles: The physicochemical properties of the developed nanoparticles such as particle size, moisture content, and morphology were examined using dynamic light scattering, moisture analyzer, scanning electron, and atomic force microscopy. Also, the biodegradation rates of the nanoparticles were estimated. Both plain and cargo (treprostinil, Selexipag, PPAR β agonists or NO donor)-loaded nanoparticles with optimum physicochemical characteristics, drug loading capacity, drug release patterns were selected for further use in the preparation of a series of novel respirable crosslinked polymeric nano-microparticles carriers.

3. Microparticle Composition

Based on our preliminary studies, the developed nanoparticles must be encapsulated or formulated into microparticles for pulmonary drug delivery due to their small aerodynamic size, which normally leads to limited deposition in the airways and extensive exhalation from the lungs following inspiration. Also, nanoparticles-based carrier systems may aggregate in both dry powder and liquid forms which causes rapid clearance by macrophage cells. This aspect of the invention develops a range of novel carrier systems for controlling drug delivery (mainly pulmonary) and combines the benefits of both polymeric nanoparticles and the respirable micron-size crosslinked hydrogel particles.

Materials: The respirable microparticles developed comprise of semi-interpenetrating polymeric networks (semi-IPNs) and full-IPNs. These semi- and full-IPNs are based mostly on natural polymers such as, but not limited to, chitosan and water soluble chitosan derivatives (such as carboxymethyl and PEGylated derivatives) in a combination with one or more of nontoxic, biocompatible, and biodegradable polymers including, but not limited to, hyaluronate, carrageenan and oligoguluronate. The semi-IPN and IPN microparticles are crosslinked through ionotropic gelation, polyelectrolyte complexation and/or H-bonding. These microparticles incorporating drug (treprostinil, Selexipag, PPAR β agonists or NO donor)-loaded nanoparticles were produced using spray-drying technique, spray gelation, and ionotropic gelation followed by lyophilization.

4. Nano-Microparticle Characterization

The design criteria of the nano-microparticle carriers requires geometric and aerodynamic particle sizes for lung delivery (1-5 μm aerodynamic diameter of dry particles), rapid dynamic swelling (>20 μm within minutes), appropriate morphology, reasonable biodegradation rates, low moisture content, high drug (treprostinil, Selexipag, PPAR β agonists or NO donor) loading efficiency and desirable drug release profiles.

The physicochemical properties of the nano-microparticles carriers, such as particle size, moisture content, and morphology were investigated with the aid of dynamic light scattering (DLS), moisture balance, scanning electron microscopy (SEM), and atomic force microscopy (AFM). Particle density and dynamic swelling were determined using pycnometer and laser diffraction, respectively. The loading capacity, and release kinetics of the incorporated treprostinil, Selexipag, PPAR β agonists or NO donor were determined. Also, the biodegradation rates of the developed formulations were measured. Based on the pre-suggested design criteria, the treprostinil-loaded nano-microparticles carriers with optimum physicochemical characteristics, high treprostinil loading efficiency, and desirable in vitro treprostinil release kinetics will be selected and optimized for further in vitro assessment of their delivery performance. Further selection and optimization of the nano-micro carriers will then determine efficacy in the treatment of PAH in an in vivo (rat) model, before further development towards human trials.

Characteristics and Potential Uses

Improving the physicochemical characteristics of treprostinil via appropriate formulation and targeting would enhance its overall target organ bioavailability.

Incorporation of treprostinil or other drugs suitable for treatment of PAH in polymeric nano-micro-carriers is advantageous over other carriers because of stability, potential for improved permeability across the physiological barriers, increased bioavailability and also reduction of undesirable side effects. In addition, the polymeric nano-micro-carriers can be designed with desirable physicochemical characteristics via the selection of appropriate candidates from a wide range of the available natural and synthetic polymers.

EXAMPLES (I) Preparation of Plain and Therapeutic agent-loaded Poly (Lactic-Co-Glycolic Acid) Nanoparticles The plain and therapeutic agents-loaded poly(lactic-co-glycolic acid) [PLGA] nanoparticles were prepared using "single Emulsion/solvent evaporation technique" through a procedure similar to that described in our previous work (see El-Sherbiny I M et al, 2010, Carbohydr Polym, 83, 1345-1354). Briefly, 1 g of PLGA was dissolved in 50 ml of methylene dichloride. Then, to this PLGA solution, 5 ml of the therapeutic agent (treprostinil, selexipag, PPAR β agonists or NO donor) solution was added with stirring. A 2.5% w/v aqueous polyvinyl alcohol (PVA) solution (70 ml) was prepared to which, the PLGA/therapeutic agent mixture was added dropwise while vortexing the capping agent (PVA) solution at high setting. The mixture was then sonicated for 2 min at 50% amplitude to create an oil-in-water emulsion. The sonication process was repeated three times until the desired size of the nanoparticles was obtained. The sonication process was performed in an ice-water bath with using pulse function (10 s pulse on, and 10 s pulse off) in order to evade the heat built-up of the PLGA/therapeutic agent solution during the sonication. Afterwards, the emulsion was immediately poured into 100 ml of an aqueous 0.3% w/v PVA solution with rapid stirring. The resulting PLGA nanoemulsion was stirred overnight in uncovered container to allow for methylene chloride and ethanol evaporation. The resulting PLGA NPs aqueous suspension was used directly or further used in the preparation of the nano-in-microparticles for inhalation. The prepared PLGA nanoparticles showed dense, compact, and integrated spherical shapes with particle radius of 247±10 and 271±18 nm for the plain and the drug-loaded PLGA nanoparticles, respectively, as determined by DLS.

(II) Preparation of Plain and Therapeutic Agent-Loaded Chitosan-Based Nanoparticles:

(1) Preparation of PEG-grafted-CS Copolymer

Figure 1:
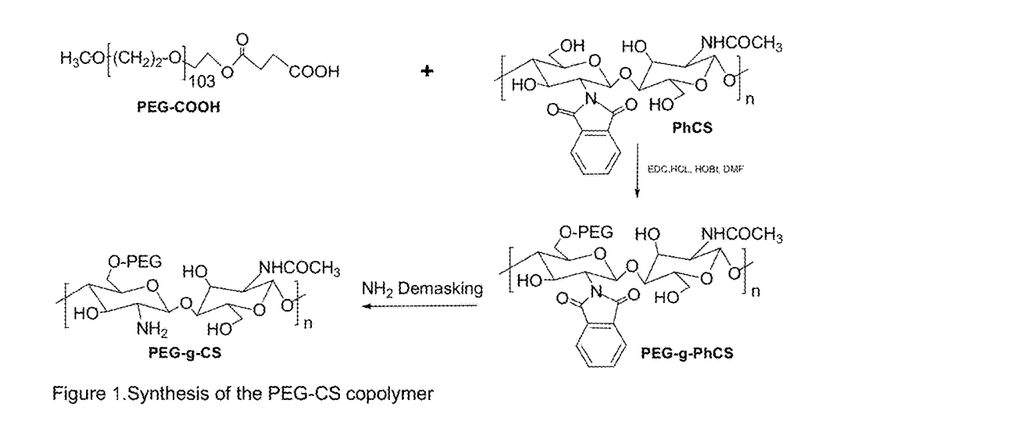
FIG. 1 shows synthesis of PEG-CS copolymers

The copolymer of PEG grafted onto CS was prepared (as illustrated in FIG. 1) by a modified method of that reported in our earlier study (El-Sherbiny, I. M., & Smyth, H. D. C. (2012). Controlled release pulmonary administration of curcumin using swellable biocompatible nano-microparticles systems. Molecular Pharmaceutics, 9(2), 269-280) and described briefly as follows:

(i) Preparation of PEG-COOH: methoxy-PEG (100 g, 20 mmol), 4-dimethylaminopyridine, DMAP (2.44 g, 20 mmol), triethylamine (2.02 g, 20 mmol), and succinic anhydride (2.4 g, 24 mmol) were dissolved in 300 ml of dry dioxane. The mixture was stirred at room temperature for 2 days under a dry nitrogen atmosphere. Dioxane was then evaporated under vacuum and the residue was taken up in $CCl_4$, filtered and precipitated by diethyl ether to produce PEG-COOH powder. (ii) Masking of the $NH_2$ groups of CS: phthalic anhydride (44.8 g, 5 molequivalent to pyranose rings) was reacted with 10 g of CS in 150 ml of DMF at 130° C. under inert atmosphere for 10 h. The resulting phthaloyl CS (PhCS) was then collected by filtration after precipitation on ice, washed extensively with methanol, and dried at 45° C. under vacuum to produce the yellowish brown PhCS. (iii) Conjugation of PEG-COOH with PhCS: PEG-COOH (37.9 g) was stirred with PhCS (5.0 g, 0.4 mol equivalent to PEG-COOH) in 70 ml of DMF. Then, 1-hydroxybenzotrizole, HOBt (3.4 g, 3 mol equivalent to PEG-COOH) was added with stirring at room temperature until a clear solution was obtained. The 1-ethyl-3-(3-dimethylaminopropyl) carbodiimide hydrochloride, EDC.HCl (4.25 g, 3 mol equivalent to PEG-COOH) was then added with stirring the mixture overnight at room temperature. A purified PEG-g-PhCS copolymer (5.47 g, white product) was obtained after dialysis of reaction mixture against distilled water followed by washing with ethanol. (iv) Demasking of PEG-g-PhCS: PEG-g-PhCS (4.1 g) was heated up to 100° C. with stirring under inert atmosphere in 20 ml of DMF. Then, 15 ml of hydrazine hydrate was added and the reaction was continued for 1.5 h. The resulting PEG-g-Cs was purified by dialysis against a (1:1) mixture of ethanol and deionized water then dried under vacuum at 45° C.

Figure 2:
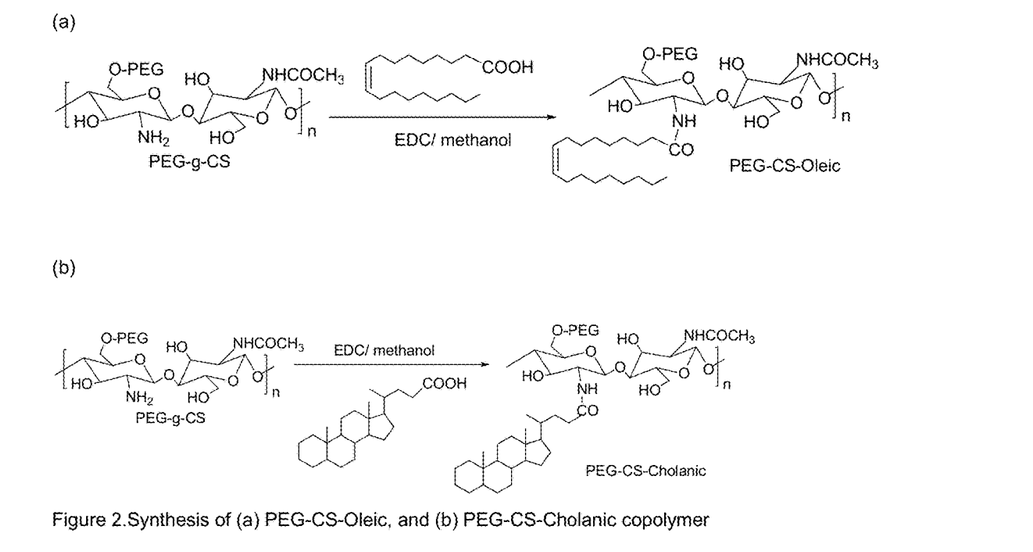
FIG. 2 shows synthesis of PEG-CS-oleic and PEG-CS-cholanic copolymers

2. Preparation of PEG-CS-Oleic and PEG-CS-Cholanic Acid Copolymers:

Hydrophobic moieties including oleic, and cholanic acid were coupled to CS backbone of the PEG-g-CS by formation of amide linkages through the EDC-mediated reaction as follows (FIG. 2): Briefly, PEG-g-CS (1 g) was dissolved in 0.6% (w/v) aqueous acetic acid solution (100 ml) and diluted with 85 ml methanol. HM was then added to PEG-g-CS solution at 0.4-0.5 mol/l glucosamine residue of CS followed by a drop-wise addition of 15 ml EDC methanol solution (0.07 g/l) while stirring at room temperature. After 20 h, the reaction mixture was added to 200 ml of methanol/ammonia solution (7/3, v/v) while stirring. The precipitated material was filtered; washed with distilled water, methanol, and ether; and then dried under vacuum for 20 h at room temperature. The DS, which represents the number of HM groups per 100 amino groups of CS, was evaluated using normal titration.

3. Characterization of the Modified Polymers:

The synthesized and chemically modified polymers used as pre-cursors for the nanoparticles fabrication were characterized using several analytical techniques such as elemental analysis (EA), Fourier transform infrared (FT-IR), nuclear magnetic resonance (NMR), differential scanning calorimetry (DSC), and thermogravimetric analysis (TGA). Also, the crystallography patterns of powdered modified polymers were investigated by X-ray diffraction (XRD).

4. FT-IR and Elemental Analysis Data of Some of the Developed Polymers and Copolymers PhCS: FT-IR ($v_{max}$, cm$^{-1}$) 3286, 2972, 1770, 1689, 1401, 1050, 727; $(C_8H_{13}NO_5)_{0.2363}(C_6H_{11}NO_4)_{0.016}(C_{14}H_{13}NO_6)_{0.747}$, calculated (%) (DS=0.97) (%): C, 55.71; H, 4.86; N, 5.21. found (%), C, 60.27; H, 4.80; N 4.97. PEG-COOH: FT-IR ($v_{max}$, cm$^{-1}$) 3502, 2879, 1743, 1114; $(C_{231}H_{461}O_{117})$, calculated (%): C, 54.38; H, 9.04. found (%), C, 56.3; H, 9.21. PEG-PhCS copolymer: FT-IR ($v_{max}$, cm$^{-1}$) 3411, 2901, 1739, 1712, 1091, 720, found EA (%), C, 56.21; H, 4.61; N, 5.22. PEG-CS copolymer: FT-IR ($v_{max}$, cm$^{-1}$) 3305, 2871, 1706, 1099. found EA (%), C, 40.51; H, 4.74; N, 14.09.

5. Development of Plain and Drug-loaded Modified CS-based Self-assembled Nanoparticles:

The developed modified CS copolymers (PEG-g-CS, PEG-CS-Oleic, and PEG-CS-Cholanic) were used to develop a new series of self-assembled nano-carrier systems for the controlled sustained delivery of treprostinil, selexipag, PPAR β agonists and NO. The nanoparticles were prepared with and without sonication of different concentrations (0.05-1.5%) of the modified polymers solutions using probe sonicator. The sonication process was performed at different sonication powers (20-45 W) for different intervals (30-120 s). The effect of relative compositions plus the different preparation parameters onto the physicochemical characteristics (particle size, morphology, drug loading capacity, and moisture content) of the resulting nanoparticles was investigated. The prepared self-assembled nanoparticles showed particle radius of 95±7 and 105±13 nm for the plain and the drug-loaded nanoparticles, respectively, as determined by DLS.

6. Development of Plain and Drug-loaded Modified CS-based Hydrogel Nanoparticles:

The prepared CS copolymers (PEG-g-CS, PEG-CS-Oleic, and PEG-CS-Cholanic) were used to develop new series of hydrogel nano-carrier systems for the controlled sustained delivery of treprostinil, selexipag, PPAR β agonists and NO. This has been achieved using various types of crosslinkers (mainly tripolyphosphate, TPP and genipin). The preparation was carried out in a mild aqueous media to ensure the stability of the loaded therapeutic agents (treprostinil, selexipag, PPAR β agonists and NO-donor). The prepared self-assembled nanoparticles showed particle radius of 295±19 and 311±24 nm for the plain and the drug-loaded nanoparticles, respectively, as determined by DLS.

7. Development of Plain and Drug-loaded Respirable Nano-microparticles:

The developed PLGA, self-assembled or hydrogel nanoparticles loaded with treprostinil, selexipag, PPAR β agonists or NO-donor were incorporated into respirable semi-interpenetrating polymeric networks (semi-IPNs) or full-IPNs microparticles. These semi- and full-IPNs were based mostly onto CS derivatives (such as N-trimethyl CS, carboxymethyl CS, and PEGylated CS) in a combination with one or more of nontoxic, biocompatible, and biodegradable polymers including, sodium alginate, hyaluronate, carrageenan and oligoguluronate. The semi-IPN and IPN microparticles were crosslinked through ionotropic gelation, polyelectrolyte complexation and/or H-bonding. The microparticles incorporating drug (treprostinil, Selexipag, PPAR β agonists or NO donor)-loaded nanoparticles were produced using spray gelation, ionotropic gelation followed by lyophilization, or spray-drying technique (NANO-01A nano-spray dryer, MECC CO., LTD., Japan). The developed nano-microparticles powder showed desirable swelling extents (10-24 times of dry size) within three minutes and also showed accepted moisture contents as dry powders (less than 1.6%), good enzymatic degradation rates, promising drug loading capacity (more than 90%), and consistent sustained release of the loaded therapeutic agents.

Experiments

Nanoparticles were prepared as described above from a combination of polymers including chitosan of low molecular weight, PEG 400 and polyvinyl pyrolidone (PVP), and other materials such as glucose and tetramethyl orthosilicate. Particles were either loaded with an NO donor (referred to as "NO nanoparticles") or not ("control" or "plain" nanoparticles). Glucose was used to perform a thermal reduction of the loaded NO-donor, sodium nitrite ($NaNO_2$) to generate NO gas. The NO remain entrapped inside the nanoparticles powder until undergoing a sustained release because of the swelling of the prepared hydrogel-based nanoparticles upon exposure to moist environment. Various nanoparticles were prepared with different concentrations of the NO-donor, sodium nitrite. In the following experiments, a sample referred to as "NO-Polymer 4" was used. This was prepared as follows: Sodium nitrite solution was prepared (1 g in 30 mM PBS at pH 7.5). Then, D-glucose was added at 40 mg D-glucose/mL of sodium nitrite solution followed by addition of PVP (6.25 mg) with stirring. Afterwards, PEG-400 was added at 0.5 mL PEG/10 mL of solution. Acidic chitosan solution (0.5% w/v) of low molecular weight was then added at a ratio of 0.5 mL/10 mL of sodium nitrite solution. In another container, acidic solution of tetramethyl orthosilicate (2.5 mL/0.6 ml HCl) was prepared and sonicated in ice bath, then added to the NO-donor solution (1 mL tetramethyl orthosilicate/10 mL solution). The resulting mixture was then stirred and set aside for gelation, followed by freeze drying. The control nanoparticles were prepared using the same procedures but without the NO-donor.

Figure 3:
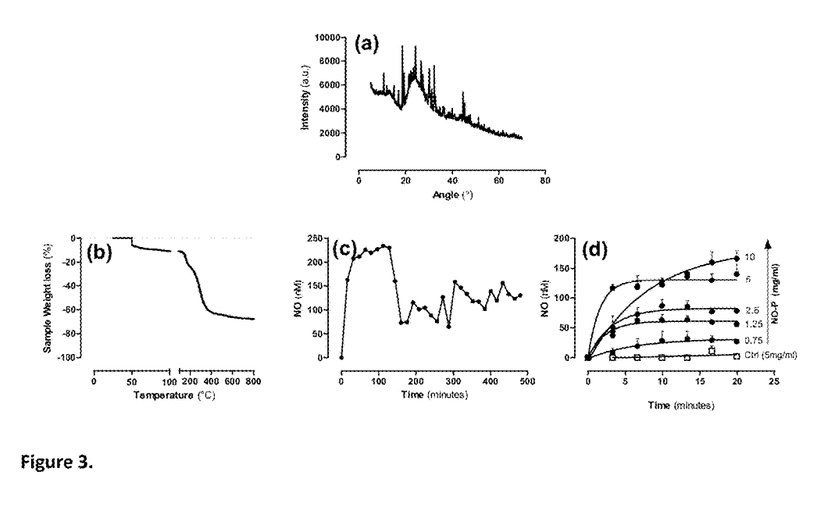
FIG. 3 shows characterization and NO release profile from NO nanoparticles

The nanoparticles were characterised by powder X-ray diffraction (FIG. 3a) and themogravimetric analysis (FIG. 3b). Particles were also assessed for NO release over a period of 8 hours (FIG. 3c) and NO release over 20 minutes from different concentrations of NO nanoparticles (0.75, 1.25, 2.5, 5, and 10 mg/ml) compared to control plain nanoparticles (at 5 mg/ml). It can be seen that the majority of NO is released in the first 100 or so minutes, while higher concentrations of nanoparticles release more NO.

Figure 4:
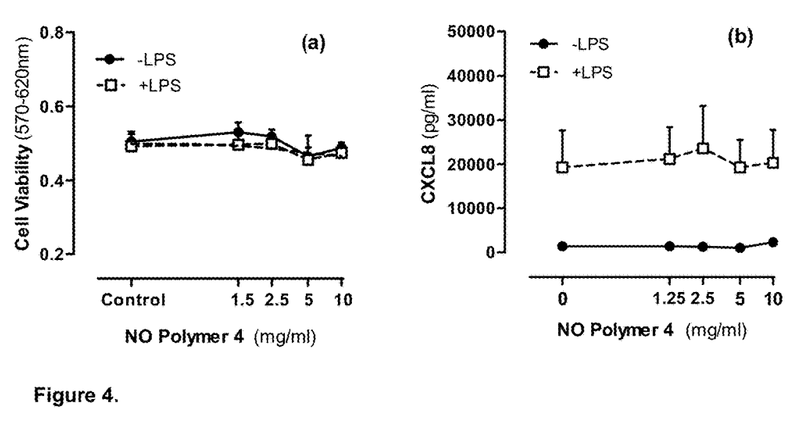
FIG. 4 shows the effect of NO nanoparticles on viability and chemokine release from endothelial cells

FIG. 4 shows the effect of the NO nanoparticles used in FIG. 3 on viability (FIG. 4a) and release of the chemokine CXCL8 (FIG. 4b) from endothelial cells grown from blood of healthy donors with or without stimulation with LPS. Nanoparticles were contacted with the cells at concentrations of 1.5, 2.5, 5, and 10 mg/ml.

Figure 5:
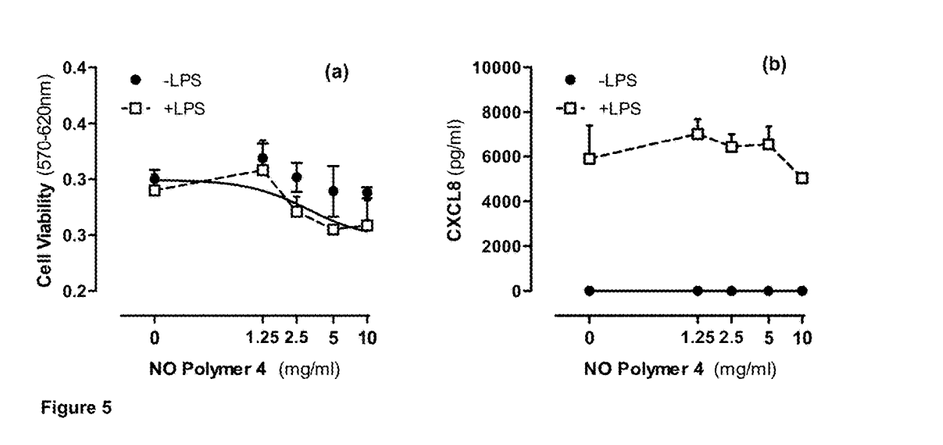
FIG. 5 shows the effect of NO nanoparticles on viability and chemokine release from arterial smooth muscle cells

FIG. 5 shows a similar experiment to FIG. 4, using pulmonary artery smooth muscle cells (PAVSMCs) in place of endothelial cells.

Figure 6:
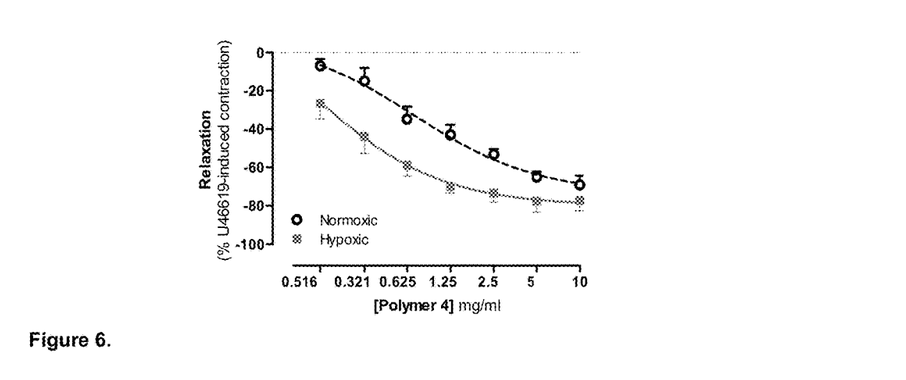
FIG. 6 shows the effect of NO nanoparticles on relaxation of pulmonary arteries in mice

FIG. 6 shows the effect of the NO nanoparticles at different concentrations on the relaxation of pulmonary arteries from control mice (normoxic) and mice with pulmonary hypertension (hypoxic). Relaxation is shown as a percentage of U46619-induced contraction. It can be seen that the NO nanoparticles induce substantial relaxation in both mouse groups.

Figure 7:
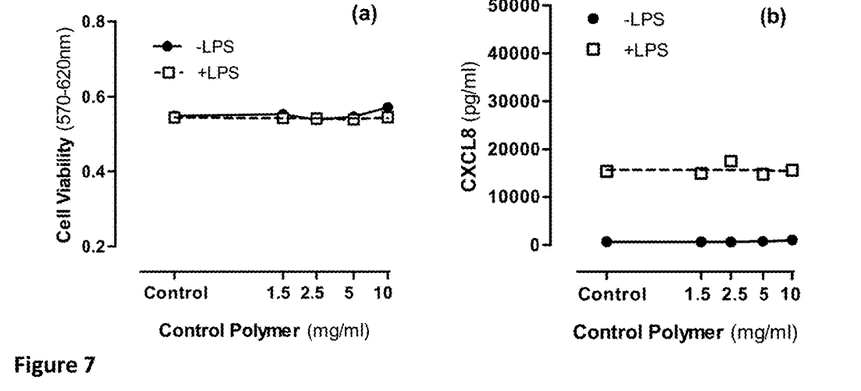
FIG. 7 shows the effect of control nanoparticles on viability and chemokine release from endothelial cells

FIG. 7 shows the effect of control nanoparticles on viability (FIG. 7a) and release of the chemokine CXCL8 (FIG. 7b) from endothelial cells grown from blood of healthy donors with or without stimulation with LPS. Nanoparticles were contacted with the cells at concentrations of 1.5, 2.5, 5, and 10 mg/ml. There is essentially no effect of the nanoparticles lacking NO.

Figure 8:
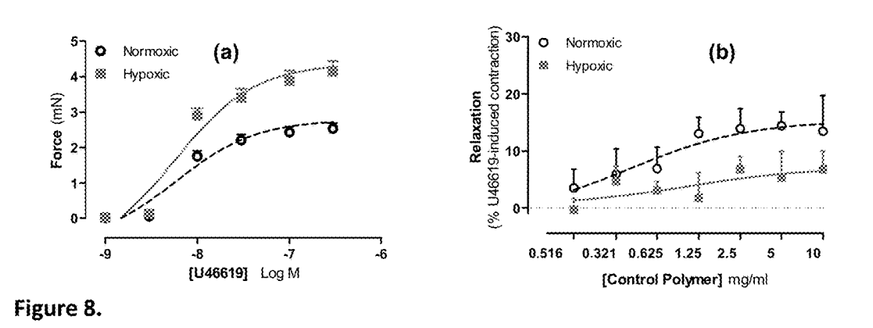
FIG. 8 shows the effect of U46619 on pulmonary arteries in mice, and the effect of control nanoparticles on mice

FIG. 8 shows the effect of U46619 on pulmonary arteries from control mice (Normoxic) and those with pulmonary hypertension (Hypoxic) (FIG. 8a), and the effect of control nanoparticles (NO-free polymer nanoparticles) on relaxing pulmonary arteries from hypoxic vs normoxic mice that have been pre-contracted with U46619 (FIG. 8b). U46619 (9,11-Dideoxy-9α,11α-methanoepoxy prostaglandin F2α) is a stable synthetic analog of the endoperoxide prostaglandin PGH2, and is a vasoconstrictor that mimics the hydroosmotic effect of vasopressin.

Figure 9:
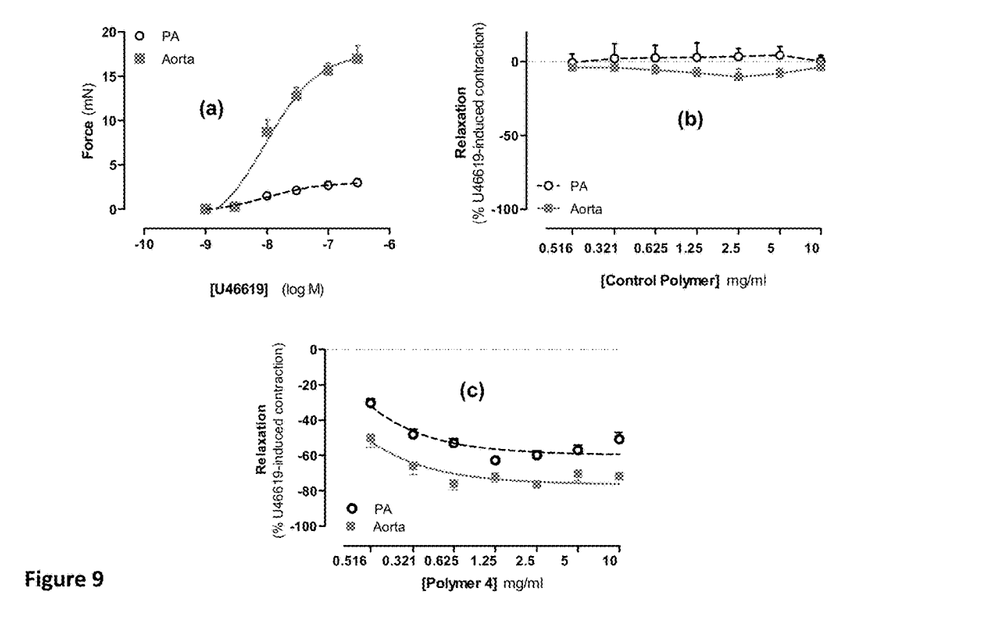
FIG. 9 shows the effect of U46619 on pulmonary arteries in mice, and the effect of control nanoparticles and NO nanoparticles on mice.

FIG. 9 shows the effect of U46619 on contractile responses of pulmonary arteries and aorta from control mice (normoxic) (FIG. 9a). There is a significant contraction of the aorta, with less contraction of the pulmonary artery. FIGS. 9b and 9c show respectively the effect of control nanoparticles (no NO) and NO nanoparticles on relaxing pulmonary arteries and aorta from control mice that have been pre-contracted with U46619. There is a substantial relaxation effect from the NO nanoparticles, which is not seen with the control nanoparticles.

Thus, these experiments demonstrate that NO-releasing agents can be incorporated into nanoparticles, and that these nanoparticles will induce relaxation of pulmonary arteries and aorta in a mouse model.

The invention claimed is:

1. A pharmaceutical formulation comprising polymeric nanoparticles encapsulated within crosslinked polymeric microparticles, wherein the polymeric nanoparticles carry a therapeutic agent suitable for treatment of pulmonary arterial hypertension (PAH) loaded within them, wherein the therapeutic agent is selected from the group consisting of a prostacyclin synthetic analog, PPAR β agonist, and NO donor, wherein the polymeric nanoparticles comprise a chitosan-derivative polymer selected from the group consisting of chitosan-PEG-Cholanic acid, chitosan-PEG-Stearic acid, and chitosan-PEG-Oleic acid, and wherein the PEG component of the polymer is connected to the chitosan component of the polymer by an ester bond, and wherein both the PEG component and the fatty acid component are connected to the same monosaccharide ring of the chitosan.

2. The formulation of claim 1, which is an inhalable, dry powder pharmaceutical formulation.

3. The formulation of claim 1, which is an oral pharmaceutical formulation.

4. The formulation of claim 1, which is an injectable pharmaceutical formulation.

5. The formulation of claim 1, wherein the nanoparticles have a mean particle diameter ranging from 1 to 500 nm.

6. The formulation of claim 5, wherein the microparticles comprise a pH responsive carrier.

7. The formulation of claim 6, wherein the crosslinked polymeric microparticles have a mean particle diameter ranging from 1 to 5 μm for inhalable formulations, and ranging from 1 to 500 μm for oral formulations.

8. The formulation of claim 1, wherein the formulation is a dry formulation and the polymeric nanoparticles have a moisture content, in the dry formulation, of less than 2%.

9. The formulation of claim 8, wherein the polymeric nanoparticles are produced via self assembly following sonication of amphiphilic polymer solutions.

10. The formulation of claim 9, wherein the crosslinked polymeric microparticles are cross-linked hydrogel polymeric microparticles.

11. The formulation of claim 10, wherein the polymeric hydrogel microparticles are pH-responsive and comprise semi-interpenetrating polymeric networks (semi-IPNs) or full-IPNs.

12. The formulation of claim 11, wherein the microparticles comprise chitosan or a water soluble chitosan derivative.

13. The formulation of claim 12, wherein the microparticles further comprise one or more polymers selected from the group consisting of hyaluronate, carrageenan, and oligoguluronate.

14. The formulation of claim 13, wherein the microparticles incorporating nanoparticles are produced using spray-drying technique, spray gelation, or ionotropic gelation followed by lyophilization.

15. The formulation of claim 14, wherein the microparticles are swellable.

16. The formulation of claim 15, wherein the microparticle is able to swell to at least 500% of the original (dry formulation) size.

17. The formulation of claim 16, wherein the formulation is an inhalable dry powder formulation, and wherein the microparticle is able to swell to a larger diameter within 10 minutes from administration to the lungs of a patient.

18. The formulation of claim 17, wherein the microparticle comprises less than 7.5% water when in the dry formulation.

19. The formulation of claim 1, wherein the therapeutic agent is a prostacyclin synthetic analog.

20. The formulation of claim 19, wherein the analog is treprostinil or selexipag.

21. A method of treating PAH, the method comprising administering a composition according to claim 1 to a subject, wherein the composition is administered to the subject by inhalation.

* * * * *